United States Patent
Zhang (10) Patent No.: US 9,453,041 B2
(45) Date of Patent: Sep. 27, 2016

(54) METHOD FOR PREPARING ALBIFLORIN AND PAEONIFLORIN

(76) Inventor: Zuoguang Zhang, Beijing (CN)

( * ) Notice: Subject to any disclaimer, the term of this patent is extended or adjusted under 35 U.S.C. 154(b) by 235 days.

(21) Appl. No.: 13/884,422

(22) PCT Filed: Nov. 10, 2010

(86) PCT No.: PCT/CN2010/078597
§ 371 (c)(1),
(2), (4) Date: May 22, 2013

(87) PCT Pub. No.: WO2012/061984
PCT Pub. Date: May 18, 2012

(65) Prior Publication Data
US 2013/0231469 A1    Sep. 5, 2013

(51) Int. Cl.
*C07H 17/04*    (2006.01)
*C07H 1/08*    (2006.01)

(52) U.S. Cl.
CPC ............... *C07H 17/04* (2013.01); *C07H 1/08* (2013.01)

(58) Field of Classification Search
None
See application file for complete search history.

(56) References Cited

FOREIGN PATENT DOCUMENTS

| CN | 1413589 | 4/2003 |
|---|---|---|
| CN | 1706397 | 2/2005 |
| CN | 1706397 | 12/2005 |
| CN | 1788753 | 6/2006 |
| CN | 101062128 | 10/2007 |
| CN | 101156863 | 4/2008 |
| CN | 101385736 | 3/2009 |
| CN | 101607975 | 12/2009 |

OTHER PUBLICATIONS

Hostettmann, K. et al., Preparative Chromatography Techniques: Applications in Natural Product Isolation, Second Edition, 1998, p. 3 and 5-9.*
Liu, Hong et al., Journal of Tianjin University of Traditional Chinese Medicine, "Study on the purification technology of radix paeoniae rubra extract by macroporous resin", 2009, English abstract.*
Shi et al., machine translation of CN101062128, original document published Oct. 2007, machine translation obtained May 14, 2015.*
Song et al., machine translation of CN1413589, original document published Apr. 2003, machine translation obtained May 14, 2015.*
Wu, Ying-haul et al., Applied Chemical Industry, "Study on extraction of paeoniflorin in Paeonia lactiflora Pall", 2007, English abstract.*
Yiyu, machine translation of CN101073606, original document published Nov. 2007, machine translation obtained May 14, 2015.*
International Search Report and Written Opinion of the International Searching Authority (PCT/CN2010/078597), Aug. 11, 2011.

* cited by examiner

*Primary Examiner* — Layla Berry
*Assistant Examiner* — Bahar Craigo
(74) *Attorney, Agent, or Firm* — Greer, Burns & Crain, Ltd.

(57) ABSTRACT

The present invention discloses a method for preparing high purity paeoniflorin and albiflorin simultaneously comprising: extraction the raw material *Paeonia Lactiflora* by percolation or heating reflux to obtain the *Paeonia Lactiflora* extract solution, then purification by macroporous absorption resin, alumina column and silica gel column in turn to obtain high purity paeoniflorin and albiflorin. The preparation method of the invention can provide high purity paeoniflorin and albiflorin with low price and energy-consumption by the identical procedure. The process is simple. The purification efficacy is high and the purification time is short.

9 Claims, 7 Drawing Sheets

Fig 1

Component table

| # | Component name | Retention time (min) | Peak height (mv) | Peak area (mv.s) | Concentration | Sample content (%) |
|---|---|---|---|---|---|---|
| 1 | paeoniflorin | 17.82 | 266.04 | 5886.90 | 0.0000 | 0.0000 |
| In total | | | 266.04 | 5886.90 | | |

Fig. 2

Component table

| # | Component name | Retention time (min) | Peak height (mv) | Peak area (mv.s) | Concentration | Sample content (%) |
|---|---|---|---|---|---|---|
| 1 | albiflorin | 14.49 | 110.66 | 1895.57 | 0.0000 | 0.0000 |
| In total | | | 110.66 | 1895.57 | | |

Fig. 3

Component table

| # | Component name | Retention time (min) | Peak height (mv) | Peak area (mv.s) | Concentration | Sample content (%) |
|---|---|---|---|---|---|---|
| 1 | paeoniflorin | 18.13 | 256.76 | 6173.67 | 0.0000 | 0.0000 |
| In total | | | 256.76 | 6173.67 | | |

Fig. 4

Component table

| # | Component name | Retention time (min) | Peak height (mv) | Peak area (mv.s) | Concentration | Sample content (%) |
|---|---|---|---|---|---|---|
| 1 | albiflorin | 13.98 | 70.39 | 1820.39 | 0.0000 | 0.0000 |
| In total | | | 70.39 | 1820.39 | | |

Fig. 5

Component table

| # | Component name | Retention time (min) | Peak height (mv) | Peak area (mv.s) | Concentration | Sample content (%) |
|---|---|---|---|---|---|---|
| 1 | paeoniflorin | 16.30 | 179.98 | 3687.08 | 0.0000 | 0.0000 |
| In total | | | 179.98 | 3687.08 | | |

Fig. 6

Component table

| # | Component name | Retention time (min) | Peak height (mv) | Peak area (mv.s) | Concentration | Sample content (%) |
|---|---|---|---|---|---|---|
| 1 | albiflorin | 12.89 | 206.64 | 3290.11 | 0.0000 | 0.0000 |
| In total | | | 206.64 | 3290.11 | | |

Fig. 7

METHOD FOR PREPARING ALBIFLORIN AND PAEONIFLORIN

This application is a U.S. National Stage under 35 U.S.C. §371 of International Application No. PCT/CN2010/078597, filed Nov. 10, 2010.

FIELD OF THE INVENTION

The invention belongs to the technical field of medicines and relates to a method for separating and extracting compounds in chemical field, in particular to a preparation process of plant natural biological active materials paeoniflorin and albiflorin.

BACKGROUND OF THE INVENTION

*Paeonia Lactiflora*, belonging to ranunculaceous paeonioideae hutch perennial herbaceous plant, and its dried roots can be used as medicine. Two kinds of peonies are recorded in Chinese Pharmacopoeia edition 2010, one of which is *Radix Paeoniae* Alba, which is dried root of *Paeoniae Lactiflora* Pall, and the other one is *Radix Paeoniae* Rubra, which is dried root of *Paeonia Veitchii* Lynch. A plurality of traditional Chinese medicinal preparations containing *Paeonia Lactiflora* appear on the market at the present time, such as anti-cerebral-thrombosis tablet, brain-benefiting and rehabilitation capsule, paralysis treating tablet, resurrecting pill, collateral activating pill and the like, which are mainly used for treating cardiovascular and cerebrovascular diseases, neuralgia, hypertension, abortion, dysmenorrhea, etc. Modern chemical research shows that: the peony mainly consists of paeoniflorin, albiflorin, oxypaeoniflorin, benzoylpaeoniflorin and other components. Owing to high content of paeoniflorin in the medicinal material, and its easy comparatively availability of the pure product, there are more reports and researches on the paeoniflorin. The paeoniflorin has activities of relieving the pain, calming, protecting the liver, resisting inflammation, regulating immune, dilating blood vessels, improving learning and memorizing behaviors and the like, and can be used for treating rheumatoid arthritis, hepatitis, senile diseases, etc. For a long time, most studies regard that the paeoniflorin, as a major active ingredient of the peony, can be taken as an index to measure the peony-containing medicine and to evaluate quality performance of the medicine depending on its content.

Albiflorin belongs to monoterpenoid compounds, the molecular formula is $C_{23}H_{28}O_{11}$, molecular weight is 480.46 and molecular structure is showed as FORMULA (I); paeoniflorin belongs to monoterpenoid compounds, the molecular formula is $C_{23}H_{28}O_{11}$, molecular weight is 480.46 and molecular structure is showed as FORMULA (II).

(I)

(II)

In recent years, modern pharmacological research found that albiflorin has functions of relieving the pain, calming and resisting convulsion, as well as function on immune system, smooth muscle, resisting inflammation and pathogenic microorganism and protecting the liver. Clinically, the albiflorin is mainly used for resisting epilepsy, relieving the pain, drug rehabilitation, reliving vertigo, treating rheumatoid arthritis, bacillary dysentery and enteritis, viral hepatitis and senile diseases, resisting barium sulfate flocculation and dissolving mucus.

Therefore, the research on albiflorin is increasing with more and more attentions. For example, a patent for invention of 200510045840.0 discloses a composition extracted and separated from *radix paeoniae* alba (*paeonia iactifora* pall), which contains active compounds paeoniflorin and albiflorin, wherein the total content of these two components is 50-95%, and the ratio of paeoniflorin to albiflorin in the composition is at 1: 10-10:1. The composition is used for preparing medicines for treating leukopenia, lower platelet and heme globin caused by various reasons. For another example, a patent for invention of 200710132810.2 discloses a pharmaceutical composition containing paeoniflorin and albiflorin, wherein the ratio of paeoniflorin to albiflorin in the composition is at 10: 1-50:1. This composition can be used for preventing and treating cardiovascular and cerebrovascular diseases. However, the above-mentioned researches are just limited in study on pharmacological effects of paeoniflorin and albiflorin, and theri product is composition of the paeoniflorin and albiflorin.

Due to chemical properties of the albiflorin, it is difficult to prepare high purity albiflorin. There is no simple and convenient technique in the existing research to prepare high purity albiflorin with low cost and large scale. For example, a patent for invention of 200910100680.3 discloses a method for preparing albiflorin by simulated moving bed chromatography (SMBC). This method used extract of total glucosides of *paeonia* as raw material and prepares the albiflorin to prepare albiflorin by SMBC, wherein. immobile phase of SMBC is C18 silica gel, and mobile phase is mixed solution of methanol or acetonitrile and water, formic acid and isopropyl alcohol. In the mixed solution, in volume percentage, the methanol or acetonitrile counts for 10-50%, the water counts for 50-90%, the formic acid counts for 0-1% and the isopropyl alcohol counts for 0-2%, and total volume percentage of the various components is 100%. The purity of the albiflorin prepared by this method can be greater than 90%, but it is not suitable for mass production, in consideration of a great amount of expense on reverse phase silica gel (RP-C18), complex procedure, strict condition control and its subsequent cost.

Therefore, there is no such a technique which can meet the need of industrial production and high-purity products of paeoniflorin and albiflorin simultaneously.

SUMMARY OF THE INVENTION

The aim of this invention is to provide a method for preparing paeoniflorin and albiflorin simultaneously, with a simple operation process and a short production cycle. In one process, using the method of the invention, paeoniflorin and albiflorin can be in kilogram-level obtained respectively. The prepared paeoniflorin and albiflorin are high in content, and the purities can be greater than 90%. Using this method to prepare paeoniflorin and albiflorin can remarkably reduce the production cost, and is applicable to massive preparation and industrial production.

To achieve the purpose, on one hand, the invention discloses a method of preparing paeoniflorin and albiflorin, which comprises the following steps sequentially:

a) percolating and extracting *Paeonia Lactiflora* by percolation extraction process to obtain *Paeonia Lactiflora* extract; and b) carrying out macroporous resin separation, alumina column chromatography and silica gel column chromatography to the *Paeonia Lactiflora* extract in turn.

Wherein, in the step a), water, ethanol or methanol is adopted as extraction solvent for said percolating and extracting, preferably water.

Specifically, the ratio of the volume of the extraction solvent to the weight of the *Paeonia lactiflora* is at 5-20:1, which is to say when the weight (dry weight) of the *Paeonia lactiflora* is 1 kg, the volume of the extraction solvent is 5-20 L, or when the weight (dry weight) of the *Paeonia lactiflora* is 1 g, volume of the extraction solvent is 5-20 ml.

In particular, in the process of percolation extraction, the ratio of flow of extraction solvent per hour to the weight of the *Paeonia lactiflora* is 0.5-8:1, preferably 1-5:1, which is to say when the weight (dry weight) of the *Paeonia lactiflora* is 1 kg, the flow of the extraction solvent per hour is 0.5-8 L, or when the weight (dry weight) of the *Paeonia lactiflora* is 1 g, the flow of the extraction solvent per hour is 0.5-8 ml.

Specifically, the method further comprises soaking the *Paeonia lactiflora* in water, then percolating and extracting, wherein ratio of the volume of the water for soaking to the weight of the *Paeonia lactiflora* is at 2-3:1, which is to say when the weight (dry weight) of the *Paeonia lactiflora* is 1 kg, the volume of the water for soaking is 2-3 L, or when the weight (dry weight) of the *Paeonia lactiflora* is 1 g, the volume of the water of soaking is 2-3 ml.

Wherein, in the step b), the macroporous resin column separation chromatography comprising step 1, step 2 and step 3:

wherein step 1 comprises adding the *Paeonia Lactiflora* extract in the macroporous resin column;

wherein step 2 comprises eluting the macroporous resin column with water as eluent, and removing impurities; and wherein step 3 comprises eluting the macroporous resin column with ethanol solution as eluent, collecting fluid from the macroporous resin column after eluting, combining paeoniflorin and/or albiflorin flows/flow in the fluid, and drying to obtain macroporous resin column separation mixture.

Specifically, in the step 1), the macroporous resin is selected from one of D101, D201, AB-8 and HP-20 nonpolar macroporous adsorption resins.

In particular, in the macroporous resin column, ratio of the volume of the macroporous adsorption resin to the weight of the *Paeonia lactiflora* is at 0.5-5:1, which is to say when the weight (dry weight) of the *Paeonia lactiflora* is 1 kg, the volume of the macroporous adsorption resin is 0.5-5 L, or when the weight (dry weight) of the *Paeonia lactiflora* is 1 g, the volume of the macroporous adsorption resin is 0.5-5 ml, preferably 1-2:1.

Specifically, in the process of macroporous resin column separation, speed of the eluting liquid is 0.5-5 times as much as the column bed volume per hour, which is to say, the fow of eluent per house is 0.5-5 times as much as the volume of the macroporous adsorption resin in the macroporous resin column.

In particular, in the macroporous resin column the flows is namely two-component flow, which containing paeoniflorin and albiflorin; the flow is namely single-component flow, which containing paeoniflorin or albiflorin.

Specifically, in the step 2), volume ratio of the water to the macroporous resin is at 3-5:1; in the step 3), the weight percentage of the ethanol solution is 30-70%, preferably 40-60%; and volume ratio of the ethanol solution to the macroporous resin is at 3-5:1.

Wherein, in the step b), the alumina column chromatography comprising step 1, step 2 and step 3:

wherein step 1 comprises dissolving the macroporous resin column separation mixture; adding aluminum oxide into the macroporous resin column separation mixture solution, and drying to obtain alumina chromatography sample;

wherein step 2 comprises arranging the alumina chromatography sample at the top of the alumina column; eluting the alumina column with ethyl acetate as eluent; collecting fluid from the alumina column after eluting; combining paeoniflorin and/or albiflorin flows/flow in the fluid, to obtain alumina chromatography eluting liquid; and wherein step 3 comprises drying the alumina chromatography eluting liquid by evaporating to obtain alumina chromatography mixture.

Specifically, in the step 1), weight ratio of the macroporous resin column separation mixture to the aluminum oxide is at 1:0.5-5; in the step 2), weight ratio of the aluminum oxide in the alumina column to the macroporous resin column separation mixture is at 5-30:1, preferably at 8-25:1, more preferably at 10-25:1.

In particular, weight ratio of the aluminum oxide added into the macroporous resin column separation mixture solution to the macroporous resin column separation mixture is at 1:0.95-1, preferably at 1:1; ratio of the diameter of the alumina column to the height of aluminum oxide in the column is at 1: 6-10.

Specifically, in the step 2), in the alumina column the flows is namely two-component flow, which containing paeoniflorin and albiflorin; the flow is namely single-component flow, which containing paeoniflorin or albiflorin.

Wherein, in the step b), the silica gel column chromatography comprising step 1, step 2 and step 3:

wherein step 1 comprises dissolving the alumina chromatography mixture, adding silica gel into the alumina chromatography mixture solution, and then drying to obtain silica gel chromatography sample;

wherein step 2 comprises arranging the silica gel chromatography sample at the top of the silica gel column; eluting the silica gel column with ethyl acetate as eluent; collecting eluting liquid; combining the flow containing paeoniflorin or albiflorin in the eluting liquid respectively; and wherein step 3 comprises respectively evaporating the flows containing paeoniflorin or albiflorin to dryness, to obtain paeoniflorin and albiflorin.

Specifically, in the step 1), weight ratio of the alumina chromatography mixture to the silica gel is at 1:0.5-5; in the step 2), weight ratio of the silica gel in the silica gel column to the alumina chromatography mixture is at 5-30:1, preferably at 12-30:1.

In particular, weight ratio of the silica gel added into the alumina chromatography mixture solution to the alumina chromatography mixture is at 1:0.95-1, preferably at 1:1; ratio of the silica gel column diameter to the height of the silica gel in the column is at 1: 6-10, preferably at 1: 8-10.

On the other hand, the invention discloses a preparation method of paeoniflorin and albiflorin, which comprises the following steps sequentially:

a) extracting *Paeonia lactiflora* by using ethanol or methanol solution as an extraction solvent with heating reflux to obtain *Paeonia lactiflora* extract;

b) removing ethanol or methanol by evaporating to concentrate the *Paeonia lactiflora* extract, diluting by water to obtain *Paeonia lactiflora* extracting diluent; and c) carrying out macroporous resin separation, alumina column chromatography and silica gel column chromatography to the *Paeonia lactiflora* extracting diluent in turn.

Wherein, in the step a), mass percentage concentration of the ethanol solution is 30-100%, and mass percentage concentration of methanol solution is 30-100%.

Specifically, in the step a), the ratio of the volume of the extracting solvent to weight (dry weight) of the medicinal material of *Paeonia lactiflora* is at 5-12:1, which is to say when weight (dry weight) of the *Paeonia lactiflora* is 1 kg, the volume of the extracting solvent is 5-12 L, or when weight (dry weight) of the *Paeonia lactiflora* is 1 g, volume of the extracting solvent is 5-12 ml; the extraction is performed for 2-3 times by 2-4 h/time.

Specifically, in the step b), ratio of the volume of the *Paeonia lactiflora* extracting diluent to the weight (dry weight) of *Paeonia lactiflora* is at 1-8:1, preferably 2-8:1, which is to say, when weight (dry weight) of the medicinal material of *Paeonia lactiflora* is 1 kg, volume of the *Paeonia lactiflora* extracting diluent is 1-8 L, or when weight (dry weight) of the *Paeonia lactiflora* is 1 g, volume of the *Paeonia lactiflora* extracting diluent is 1-8 ml.

Specifically, in the step c), the macroporous resin column chromatography comprising step 1, step 2 and step 3:

wherein step 1 comprises adding the *Paeonia lactiflora* extracting diluent in the macroporous resin column;

wherein step 2 comprises eluting the macroporous resin column with water as eluent, and removing impurities; and wherein step 3 comprises eluting the macroporous resin column with ethanol solution as eluent, collecting fluid from the macroporous resin column after eluting, combining paeoniflorin and/or albiflorin flows/flow in the fluid, and then drying to obtain macroporous resin column separation mixture.

Specifically, in the step c), the alumina column chromatography including step 1, step 2 and step 3:

wherein step 1 comprises dissolving the macroporous resin column separation mixture; adding aluminum oxide into the macroporous resin column separation mixture solution, and drying to obtain alumina chromatography sample;

wherein step 2 comprises arranging the alumina chromatography sample at the top of the alumina column; eluting the alumina column by using ethyl acetate as eluent; collecting fluid from the alumina column after eluting; combining paeoniflorin and/or albiflorin flows/flow in the fluid, to obtain alumina chromatography eluting liquid; and wherein step 3 comprises drying the alumina chromatography eluting liquid by evaporating to obtain alumina chromatography mixture.

Specifically, in the step c), the silica gel column chromatography including step 1, step 2 and step 3:

wherein step 1 comprises dissolving the alumina chromatography mixture, adding silica gel into the alumina chromatography mixture solution, and then drying to obtain silica gel chromatography sample;

wherein step 2 comprises arranging the silica gel chromatography sample at the top of the silica gel column; eluting the silica gel column by using ethyl acetate as eluent; collecting eluting liquid (namely flowing liquid or effluent); combining the flows/flow containing paeoniflorin or albiflorin flow in the eluting liquid; and wherein step 3 comprises respectively evaporating the flows/flow containing paeoniflorin or albiflorin to dryness, to obtain paeoniflorin and albiflorin respectively.

The invention has the following advantages:

1. The method disclosed by the invention can prepare paeoniflorin and albiflorin in a same process, and can respectively prepare kilogram-level paeoniflorin and kilogram-level albiflorin; the method makes full use of comprehensive use value of the medicinal resource, and is suitable for industrial production.

2. The paeoniflorin and albiflorin prepared by the method disclosed by the invention are high in purity, and the content of paeoniflorin and albiflorin content is more than 90% after being purified by silica gel column chromatography.

3. Taking water as extraction solvent to extrating paeoniflorin and albiflorin in the invention, and using nontoxic and harmless ethanol and ethyl acetate as purified eluting solvent, so not only is the cost saved, but the method is environmental-friendly, and meets development demands of green economy and environmental protection.

4. The preparation method disclosed by the invention is simple in process, high in refining efficiency, low in energy consumption, environmental-friendly, easy in control of operation process conditions and qualities.

5. High purity paeoniflorin and albiflorin of the invention can be independently used for preparing medicines and functional healthcare foods, or combined with any other traditional Chinese and Western medicines or foods, in particular some traditional Chinese medicines capable of activating blood and removing stasis and treating cardiovascular and cerebrovascular diseases or traditional Chinese medicines capable of calming and resisting depression and anxiety, to take a cooperative or synergistic effect, for preparing medicines or functional healthcare foods.

DESCRIPTION OF THE EMBODIMENTS

The invention will be further described by embodiments below, and advantages and characteristics of the invention will be clearer with the description. But the embodiments are just for demonstration, and not limit scope of the invention. Technicians of the field shall understand that modifications or replacements on details and forms of the technical scheme without deviation away from spirit and scope of the invention are permitted, but the modifications and replacements shall be included within the protection scope of the invention.

Embodiment 1

1. Extraction of Medicinal Material 1) crushing 3 kg of dried *Radix Paeoniae* Alba into coarse powder, adding the powder in a stainless steel tank (volume is 12 L) for percolating traditional Chinese medicine, and then adding 6 L purified water in the tank to soak the *Radix Paeoniae* Alba for 2 h.

2) using purified water to percolate and extract the coarse powder, to obtain *Radix Paeoniae* Alba extract, wherein flow speed of the solvents in extraction is 6 L/h, and ratio of volume of the purified water to the weight of the medicinal material *Radix Paeoniae* alba is at 10:1, which is to say when weight (dry weight) of the *Radix Paeoniae* alba is 1 kg, volume of the purified water is 10 L, or when weight (dry weight) of the *Radix Paeoniae* alba is 1 g, volume of the purified water is 10 ml.

2. Macroporous Resin Column Chromatography 1) adsorbing and separating the *Radix Paeoniae* Alba extract by macroporous absorption resin, wherein the macroporous absorption resin is D101 macroporous resin, column volume of D101 macroporous absorption resin in the macroporous absorption resin column is 4 L (chromatography column is 8 cm in diameter and 1.5 m high), ratio of volume of resin to weight (dry weight) of the medicinal material *Radix Paeoniae* Alba is at 4:3, which is to say when weight (dry weight) of *Radix Paeoniae* Alba is 3 kg, the volume of the macroporous resin is 4 L, or when weight (dry weight) of *Radix Paeoniae* Alba is 30 g, the volume of the macroporous resin is 40 ml; after the *Radix Paeoniae* Alba extract completely flows into the resin column at speed of 8 L/h, eluting by 12 L of purified water until the fluid (namely flowing liquid or effluent, which being eluted from the macroporous absorption resin column) is clear, and discarding the flowing liquid after being eluted from the resin column by water; eluting by 12 L of ethanol which is 50% by weight percentage at speed of 8 L/h; collecting the flowing liquid after being eluted from the resin column by ethanol, wherein every 3 L of flowing liquid is collected as one flow part;

2) detecting paeoniflorin and albiflorin in the collected macroporous resin column ethanol eluting flow parts by thin-layer chromatography (TCL), combining the eluent flow part containing paeoniflorin and/or albiflorin, to obtain resin column efflux, wherein in the TLC, silica gel G board is taken as thin-layer board, and mixing liquid of chloroform and methanol which are mixed in the ratio of 4:1 by volume is taken as solvent for TLC; after chromatography, spraying 5% of ethanol-sulfate solution, heating for 5 min at 150° C. for colour development; and 3) condensing the resin column efflux containing paeoniflorin and albiflorin by using a vacuum condensing tank to remove the solvent; and evaporating further by water-bath, and the grinding the residue to obtain 210 g of macroporous resin column separation mixture, wherein the process of condensing is performed at 70° C., with a relative pressure of −0.09~−0.075 MPa.

3. Alumina Column Chromatography 1) completely dissolving the macroporous resin column separation mixture by proper amount of methanol, adding 210 g of aluminum oxide powder (100-200 meshes), uniformly stirring, drying and grinding to obtain alumina column chromatography sample;

2) arranging the alumina column chromatography sample at the top of the alumina column, and implementing alumina column chromatography by taking ethyl acetate as eluent, wherein granularity of absorber aluminum oxide in the alumina column is 100-200 meshes, ratio of the diameter of the alumina column to the height of aluminum oxide in the column is at 1:10, weight ratio of the absorber aluminum oxide to the macroporous resin column separation mixture is at 20:1; the ethyl acetate is taken as eluent by dosage of 100 L, and every 1 L of fluid (namely flowing liquid or effluent, which being eluted from the alumina column) is collected as one flow part;

3) detecting paeoniflorin and albiflorin in the collected alumina column ethanol eluting flow part by thin-layer chromatography (TLC), combining the eluting flow part containing paeoniflorin and/or albiflorin, to obtain alumina chromatography efflux, wherein in the TLC, silica gel G board is taken as thin-layer board, and mixing liquid of chloroform and methanol which are mixed in the ratio of 4:1 by volume is taken as solvent systems for TLC; after chromatography, spraying 5% of ethanol-sulfate solution, heating for 5 min at 150° C. for colour development; and 4) condensing the alumina chromatography effluex by evaporation to obtain 121 g of alumina chromatography mixture.

4. Silica Gel Column Chromatography 1) dissolving alumina chromatography mixture by ethanol of 95% by weight percentage, adding 120 g of silica gel powder (200-300 mesh), uniformly stirring, drying and grinding to obtain silica gel chromatography sample;

2) arranging the silica gel chromatography sample on the top of the silica gel column, and carrying out silica gel column chromatography by taking ethyl acetate as eluent, wherein particle size of absorber silica gel in the silica gel column is 100-200 mesh, ratio of the diameter of the silica gel column to the height of silica gel in the column is at 1:10, weight ratio of the absorber silica gel to the alumina chromatography mixture is at 24:1, and flow speed is 10 L/h; the ethyl acetate is taken as eluent by dosage of 96 L, and every 1 L of fluid (namely flowing liquid or effluent, which being eluted from the silica gel column) is collected as one flow part;

3) detecting contents of paeoniflorin and albiflorin in the collected silica gel column eluting flow part by thin-layer chromatography (TLC), combining the eluting flow part only containing paeoniflorin as the first part (namely paeoniflorin part), and combining the eluting flow part only containing albiflorin as the second part (namely albiflorin part), wherein in the TLC, silica gel G board is taken as thin-layer board, and mixing liquid of chloroform and methanol which are mixed in the ratio of 4:1 by volume is taken as solvent systems for TLC; after chromatography, spraying 5% of ethanol-sulfate solution, heating for 5 min at 150° C. for colour development; and 4) respectively drying two combined parts by evaporation to obtain 83.9 g of paeoniflorin and 25.3 g of albiflorin.

The contents of the prepared paeoniflorin and albiflorin are detected by HPLC. The detection conditions are as follows: instrument: Water 515 pump, 2487 detector; spectrum column: Hyper ODS2 C18; mobile phase: mixture of acetonitrile: 0.1% of phosphoric acid solution (14:86); detection wavelength: 230 nm; and flow speed: 1.0 ml/min.

Figure 1:
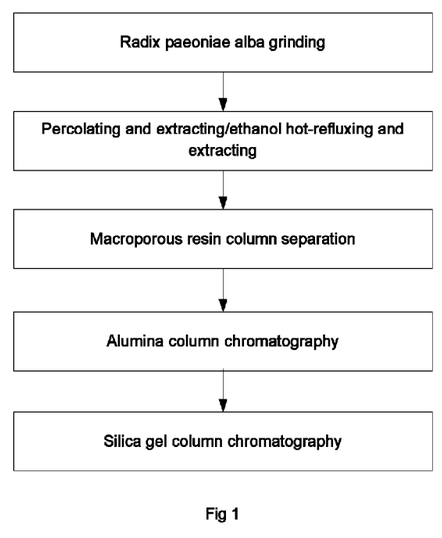
FIG. 1. is a flow chart of preparing paeoniflorin and albiflorin.
Figure 2:
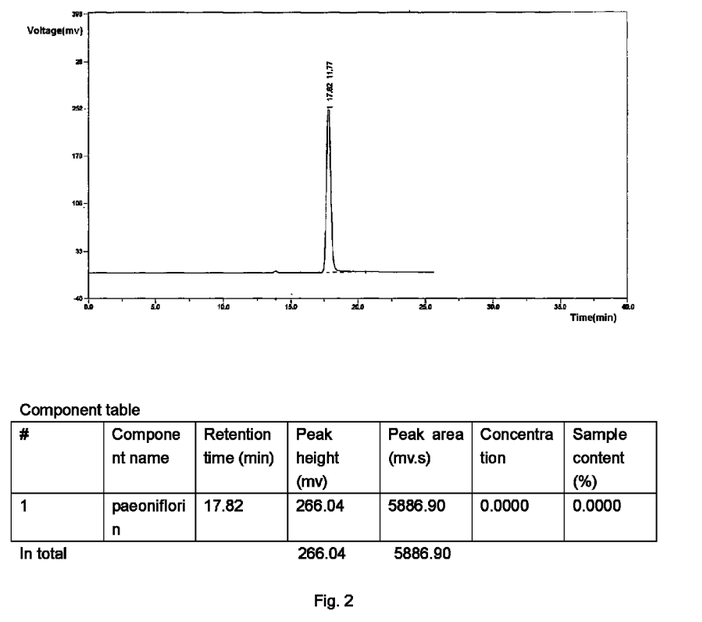
FIG. 2. is a HPLC chromatogram of paeoniflorin prepared by embodiment 1.
Figure 3:
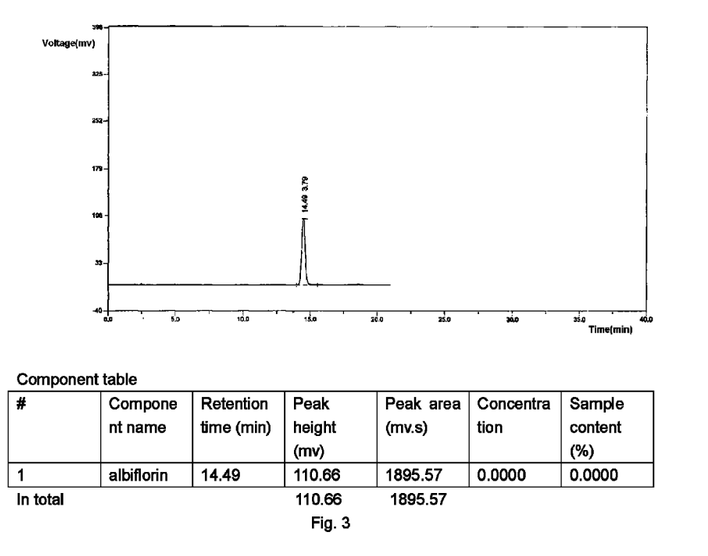
FIG. 3. Is a HPLC chromatogram of albiflorin prepared by embodiment 1.

After HPLC determination, the content of paeoniflorin is 96.7%, see FIG. 2, and the content of albiflorin is 98.6%, see FIG. 3.

Embodiment 2

In the process of extraction of the medicinal material, except for that ratio of the volume of the extraction solvent of purified water to the weight of the medicinal material *Radix Paeoniae* alba is at 5:1 and flow speed of the purified water is 4 L/h, others are identical to the embodiment 1;

In the process of macroporous resin column chromatography, except for that the macroporous absorption resin is HP-20 macroporous resin, ratio of volume of resin to weight (dry weight) of the medicinal material of *Radix Paeoniae* alba is at 1:1, mass percentage concentration of the eluent ethanol is 30% and dosage is 20 L, and 189 g of macroporous resin column separation mixture is obtained, other operations are same as in the embodiment 1;

In the process of alumina column chromatography, except for that weight ratio of the absorber aluminum oxide to the macroporous resin column separation mixture is at 10:1, ratio of the diameter of the alumina column to the height of the aluminum oxide in the column is at 1:6; dosage of the ethyl acetate is 53 L, eluting flow speed is 8 L/h, and 105 g of alumina chromatography mixture is obtained, others are identical to the embodiment 1;

In the process of silica gel column chromatography, except for that weight ratio of the absorber silica gel to the alumina chromatography mixture is at 15:1, the ethyl acetate is taken as eluent by dosage of 62 L, eluting flow speed is 6 L/h, ratio of the column diameter of the silica gel column to the height of the silica gel in the column is at 1:10, 74.3 g of paeoniflorin is obtained, and 23.6 g of albiflorin is obtained, others are identical to the embodiment 1.

After HPLC determination, the content of paeoniflorin is 92.7%, and albiflorin content is 93.6%.

Embodiment 3

In the process of percolating and extracting the medicinal material, except for that ratio of the volume of the extraction solvent of purified water to the weight of the medicinal material *Radix Paeoniae* alba is at 15:1 and flow speed of the purified water is 3 L/h, other operations are identical to the ones in embodiment 1;

In the process of macroporous resin column chromatography, except for that the macroporous absorption resin is D-201 macroporous resin, ratio of volume of resin to weight (dry weight) of the medicinal material of *Radix Paeoniae* alba is at 5:3, mass percentage concentration of the eluent ethanol is 70% and dosage is 12 L, eluting flow speed is 4 L/h, and 243 g of macroporous resin column separation mixture is obtained from macroporous resin column separation, others are identical to the embodiment 1;

In the process of alumina column chromatography, except for that weight ratio of the absorber aluminum oxide to the macroporous resin column separation mixture is at 25:1, dosage of the ethyl acetate is 168 L, eluting flow speed is 8 L/h, and 124 g of alumina chromatography mixture is obtained, others are identical to the embodiment 1;

In the process of silica gel column chromatography, except for that weight ratio of the absorber silica gel to the alumina chromatography mixture is at 30:1, the ethyl acetate is taken as eluent by dosage of 120 L, eluting flow speed is 6 L/h, 84.3 g of paeoniflorin is obtained, and 27.9 g of albiflorin is obtained, others are identical to the embodiment 1.

After HPLC determination, the content of paeoniflorin is 97.5%, and the content of albiflorin content is 96.7%.

Embodiment 4

1. Extraction of Medicinal Material 1) crushing 1 kg of dried *Radix Paeoniae* alba into coarse powder, adding in a round-bottom flask of 10 L; heating, and refluxing and extracting by ethanol as extraction solvent for three times, wherein weight percentage concentration of the extracting solvent ethanol is 50%, dosages of ethanol for three times of extraction are respectively 5 L, 5 L and 5 L, and three times of extraction respectively last for 3 h, 3 h and 2 h;

2) combining *Radix Paeoniae* alba extracting liquid of three times; arranging the liquid into a vacuum condensing tank (produced by Wuxi Huaxin Pharmaceutical Equipment Co., Ltd.); removing ethanol, condensing the above-mentioned liquid by evaporating ethanol until there is no ethanol to obtain *Radix Paeoniae* alba concentrate, wherein the process of condensing is performed at 70° C., with a relative vacuum degree of −0.09~−0.075 MPa;

3) adding purified water into the *Radix Paeoniae* alba concentrate until the total volume is 2 L to obtain *Radix Paeoniae* alba extracting diluent for further use, wherein the ratio of the volume of the *Radix Paeoniae* alba extracting diluent to the weight of the *Radix Paeoniae* alba is at 2:1.

Besides the extraction solvent in the process of heating, refluxing and extracting is 50% ethanol solution, other ethanol solutions with weight percentage ranging from 30% to 100% are applicable to the invention.

2. Macroporous Resin Column Chromatography 1) adsorbing and separating the *Radix Paeoniae* rubra extracting diluent by macroporous absorption resin, wherein the macroporous absorption resin is D-201 macroporous resin, column volume of D-201 macroporous absorption resin in the macroporous absorption resin column is 1.5 L (chromatography column is 5.5 cm in diameter and 1200 cm high), ratio of volume of resin to weight (dry weight) of the medicinal material of *Radix Paeoniae* rubra is at 1.5:1, which is to say when weight (dry weight) of *Radix Paeoniae* rubra is 1 kg, the volume of the macroporous resin is 1.5 L; after the *Radix Paeoniae* rubra extracting diluent completely flows into the resin column at speed of 1 L/h, eluting by 5 L of purified water until the fluid (namely flowing liquid or effluent, which being eluted from the macroporous absorption resin column) is clear, and discarding the flowing liquid after being eluted from the resin column by water; eluting by 5 L of ethanol which is 50% by weight percentage at flow speed of 1.5 L/h; collecting the fluid after being eluted from the resin column by ethanol; and 2) condensing resin column eluent containing paeoniflorin and albiflorin by using a vacuum condensing tank; after condensing, evaporating by water bath and grinding to obtain 71 g of macroporous resin column separation mixture, wherein the process of condensing is performed at 70° C., with a relative pressure of −0.09~−0.075 MPa.

3. Alumina Column Chromatography

Except for that weight ratio of the absorber aluminum oxide to the macroporous resin column separation mixture is at 8:1, diameter of alumina chromatography column is 5.5 cm, the ratio of the diameter of the alumina column to the height of the aluminum oxide in the column is at 1:10; dosage of the ethyl acetate is 48 L, speed of eluting is 4 L/h, and 41 g of alumina column chromatography mixture is obtained, other operations are same as in the embodiment 1.

4. Silica Gel Column Chromatography

Except for that weight ratio of the absorber Silica gel to the alumina column chromatography mixture is at 12:1, diameter of the Silica gel chromatography column is 7.6 cm, ratio of the diameter of the silica gel column to the height of the silica gel in the column is at 1:10, the ethyl acetate is taken as eluent by dosage of 36 L, speed of eluting is 3 L/h, 26.13 g of paeoniflorin is obtained, and 9.12 g of albiflorin is obtained, other operations are same as in the embodiment 1.

Figure 4:
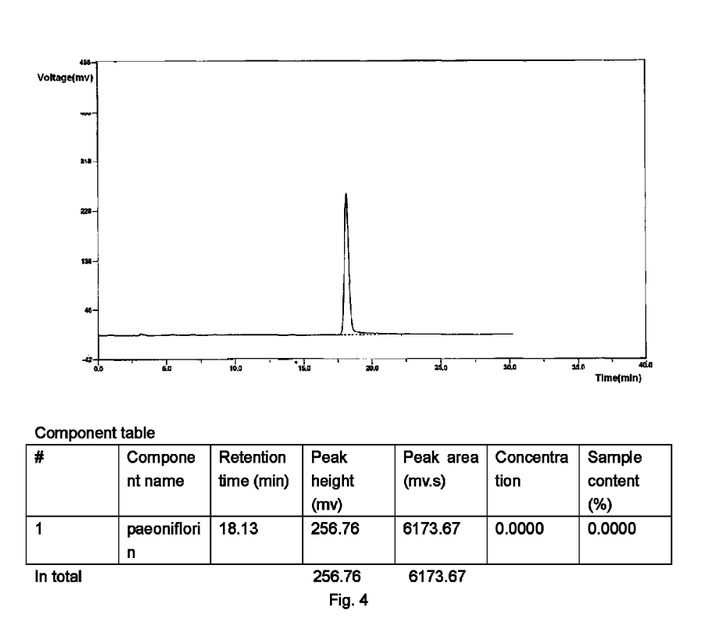
FIG. 4. is a HPLC chromatogram of paeoniflorin prepared by embodiment 4.
Figure 5:
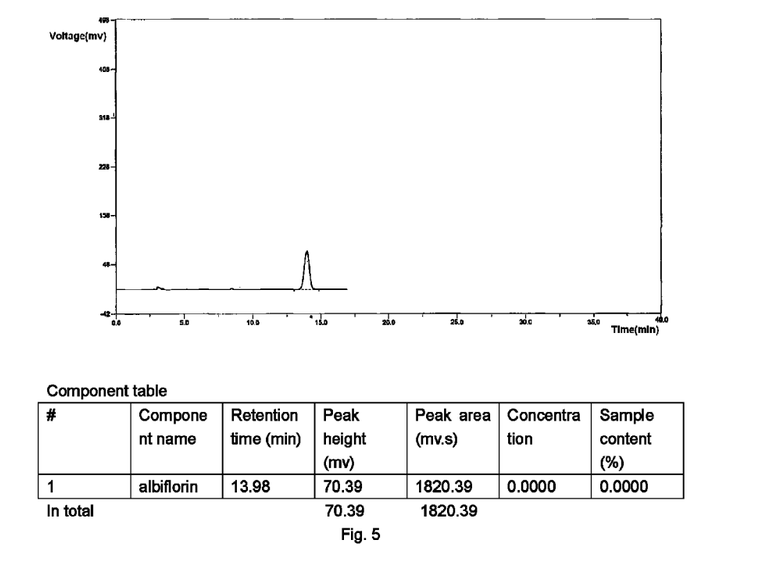
FIG. 5. is a HPLC chromatogram of albiflorin prepared by embodiment 4.

After HPLC determination, the content of paeoniflorin is 94.05%, see FIG. 4, and the content of albiflorin is 92.25%, see FIG. 5.

Embodiment 5

In the process of extraction of the medicinal material, except for that the extraction solvent is ethanol solution of 70% by weight percentage concentration, the process of refluxing and extracting is performed twice by dosage of extraction solvent ethanol as 12 L and 10 L for 4 h and 3 h, the *Radix Paeoniae* rubra extracting liquid is condensed and the ethanol is recovered, and the purified water is added into the *Radix Paeoniae* rubra concentrate to obtained *Radix Paeoniae* rubra extracting diluent which total volume is 8 L, other operations are identical to embodiment 4;

In the process of macroporous resin column chromatography, except for that the macroporous absorption resin is AB-8 macroporous resin, ratio of volume of resin to weight (dry weight) of the *Radix Paeoniae* rubra is at 2:1; the *Radix Paeoniae* rubra extracting diluent completely flows into the resin column at 2 L/h and is eluted by 8 L purified water; weight percentage concentration of the ethanol solution is 70% and dosage is 6 L, speed for eluting is 2 L/h, and 83 g of macroporous resin column separation mixture is obtained, other operations are identical to the embodiment 1;

In the process of alumina column chromatography, except for that weight ratio of the absorber aluminum oxide to the macroporous resin column separation mixture is at 20:1, diameter of alumina chromatography column is 7.6 cm, ratio of the column diameter to the height of the aluminum oxide in the alumina column is at 1:10; dosage of the ethyl acetate is 66 L, eluting flow speed is 4 L/h, and 37.2 g of alumina chromatography mixture is obtained, others are identical to the embodiment 1;

In the process of silica gel column chromatography, except for that weight ratio of the absorber silica gel to the alumina chromatography mixture is at 28:1, diameter of the silica gel chromatography column is 10 cm, ratio of the column diameter to the height of the silica gel in the column is at 1:10, the ethyl acetate is taken as eluent by dosage of 86 L, eluting flow speed is 3 L/h, 25.12 g of paeoniflorin is obtained, and 8.38 g of albiflorin is obtained, others are identical to the embodiment 1.

Figure 6:
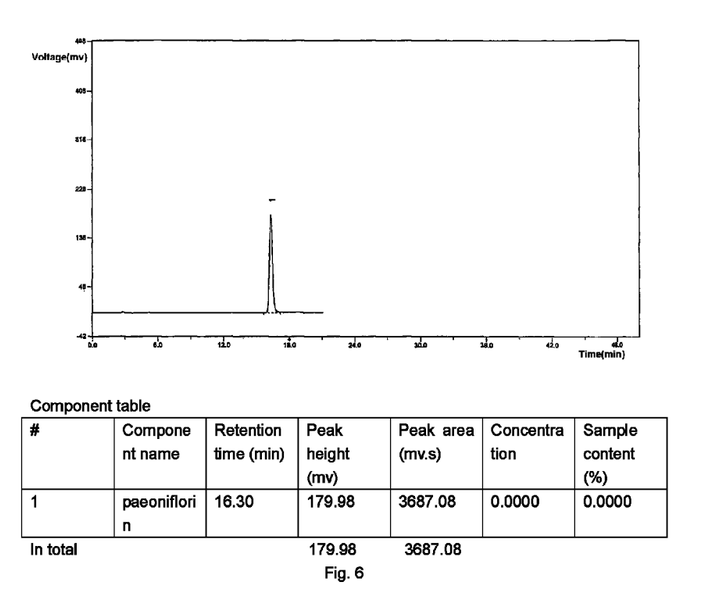
FIG. 6. is a HPLC chromatogram of paeoniflorin prepared by embodiment 5.
Figure 7:
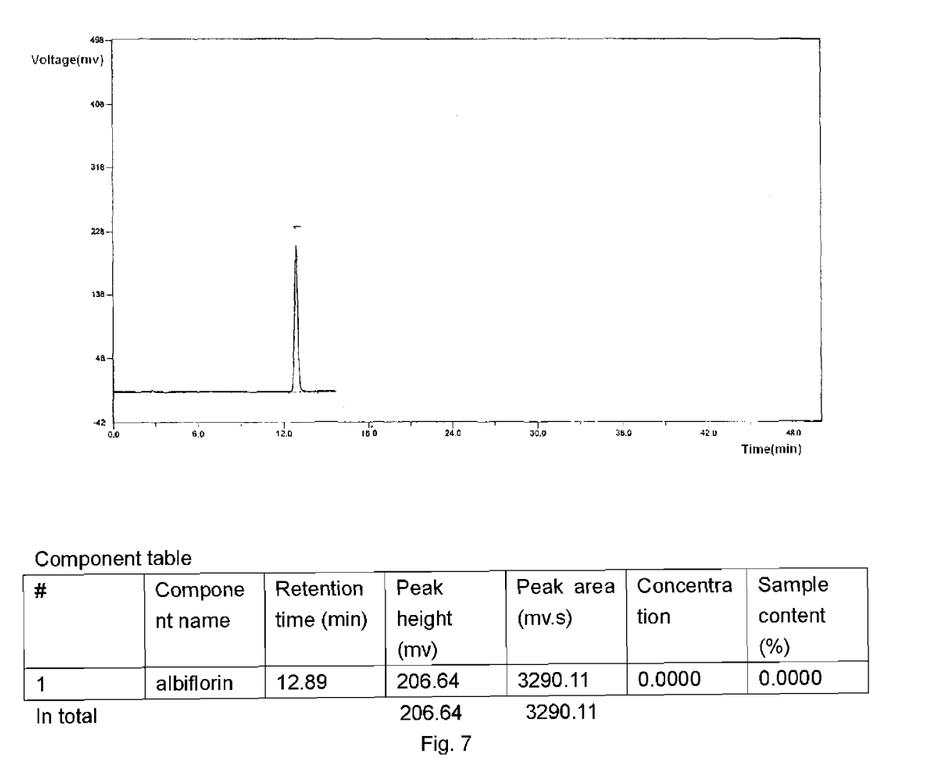
FIG. 7. is a HPLC chromatogram of albiflorin prepared by embodiment 5.

After HPLC determination, the content of paeoniflorin is 98.5%, see FIG. 6, and the content of albiflorin is 94.1%, see FIG. 7.

The invention claimed is:

1. A preparation method of paeoniflorin and albiflorin, which comprises the following steps:
   a) percolating and extracting *Paeonia Lactiflora* by percolation extraction process to obtain *Paeonia Lactiflora* extract; and
   b) carrying out macroporous resin column chromatography to the *Paeonia Lactiflora* extract to obtain macroporous resin column separation mixture;
   c) carrying out alumina column chromatography to the macroporous resin column separation mixture, wherein the alumina column chromatography comprises:
   c-1) dissolving the macroporous resin column separation mixture; adding aluminum oxide into the macroporous resin column separation mixture solution, and drying to obtain alumina chromatography sample;
   c-2) arranging the alumina chromatography sample at the top of the alumina column; eluting the alumina column with ethyl acetate as eluent; collecting fluid from the alumina column after eluting; combining paeoniflorin and/or albiflorin flows/flow in the fluid, to obtain alumina chromatography eluting liquid; and
   c-3) drying the alumina chromatography eluting liquid to obtain alumina chromatography mixture;
   d) carrying out silica gel column chromatography to the alumina chromatography mixture, wherein the silica gel column chromatography comprises:
   d-1) dissolving the alumina chromatography mixture, adding silica gel into the alumina chromatography mixture solution, and then drying to obtain silica gel chromatography sample;
   d-2) arranging the silica gel chromatography sample at the top of the silica gel column; eluting the silica gel column with ethyl acetate as eluent; collecting fluid from the silica gel column after eluting; combining paeoniflorin or albiflorin flow in the fluid respectively; and
   d-3) evaporating the flows containing paeoniflorin or albiflorin to dryness respectively, to obtain two separate products; paeoniflorin and albiflorin.

2. The preparation method as claimed in claim 1, wherein in the step a), water, ethanol or methanol is adopted as extraction solvent for said percolating and extracting.

3. The preparation method as claimed in claim 2, wherein the ratio of the volume of the extraction solvent to the weight of the *Paeonia lactiflora* is 5-15:1.

4. The preparation method as claimed in claim 1, wherein in the step b), the macroporous resin column chromatography comprises:
   b-1) adding the *Paeonia lactiflora* extract in the macroporous resin column;
   b-2) eluting the macroporous resin column with water as eluent; and
   b-3) eluting the macroporous resin column with ethanol solution as eluent, collecting fluid from the macroporous resin column after eluting, combining paeoniflorin and/or albiflorin flows/flow in the fluid, and drying to obtain macroporous resin column separation mixture.

5. The preparation method as claimed in claim 4, wherein in the step b-1), the macroporous resin is selected from one of D101, D201, AB-8 and HP-20 nonpolar macroporous adsorption resins.

6. The preparation method as claimed in claim 4, wherein ratio of the volume of the macroporous adsorption resin to the weight of the *Paeonia lactiflora* is at 0.5-5:1.

7. The preparation method as claimed in claim 4, wherein in the step b-3), the weight percentage of ethanol solution is 30-70%.

8. The preparation method as claimed in claim 1, wherein in the step c-2), the weight ratio of the aluminum oxide in the alumina column to the macroporous resin column separation mixture is at 5-30:1.

9. The preparation method as claimed in claim 1, wherein in the step d-2), the weight ratio of the silica gel in the silica gel column to the alumina chromatography mixture is at 5-30:1.

* * * * *